United States Patent [19]

Lahodny et al.

[11] Patent Number: 4,644,953
[45] Date of Patent: Feb. 24, 1987

[54] SURGICAL INSTRUMENT, MORE PARTICULARLY HYSTERECTOMIUM

[75] Inventors: Johann Lahodny, Gmünd, Austria; Ernst Dreier, Steckborn, Switzerland

[73] Assignee: Fritz Gegauf AG Bernina Nähmaschinen Fabrik, Steckborn, Switzerland

[21] Appl. No.: 644,782

[22] Filed: Aug. 27, 1984

[30] Foreign Application Priority Data

Sep. 13, 1983 [CA] Canada ........................................ 4927

[51] Int. Cl.⁴ .............................................. A61F 17/32
[52] U.S. Cl. .................................. 128/305; 128/340; 128/361; 128/321
[58] Field of Search ................ 128/340, 305, 311, 321, 128/361, 334 R; 112/169, 164

[56] References Cited

U.S. PATENT DOCUMENTS

| Re. 14,923 | 7/1920 | Smit | 128/340 |
| 1,918,700 | 7/1933 | Harris | 128/305 |
| 1,933,024 | 10/1933 | Nagelmann | 128/334 R |
| 2,264,679 | 12/1941 | Ravel | 128/340 |
| 4,325,314 | 4/1982 | Niem | 112/199 |

FOREIGN PATENT DOCUMENTS

| 134750 | 3/1985 | European Pat. Off. | 128/321 |
| 81/01958 | 7/1981 | PCT Int'l Appl. | 128/305 |

Primary Examiner—Robert P. Swiatek
Assistant Examiner—Cary E. Stone
Attorney, Agent, or Firm—Marmorek, Guttman & Rubenstein

[57] ABSTRACT

The hysterectomium comprises beside of clamping jaws on one side of the clamping jaws a cutting blade for cutting of tissue and on the other side of the clamping jaws a stitching device. The instrument permits a particularly rational working during which sections of tissue are clamped, sutured on one side and separated at the side.

13 Claims, 16 Drawing Figures

SURGICAL INSTRUMENT, MORE PARTICULARLY HYSTERECTOMIUM

BACKGROUND OF THE INVENTION

The present invention relates to a surgical instrument, more particularly a hysterectomium for clamping, ligating and severing of tissue. A hysterectomium is more particularly adapted for the surgical removal of the uterus. Known intrumentarium comprise specialized instruments like hysterectomium forceps for clamping of tissue (DE-A-30 13 836), scissors for cutting tissue's parts and suturing apparatuses of all kinds. The work at the time of an operation e.g. the removal of the uterus is rendered considerably more difficult due to the fact that the various instruments are applied one after the other, in part also together, at the same place. More particularly the suturing procedure is difficult and time consuming because suturing points must be executed at the side of the forceps when the latter is locked in the clamping position. Attempts have been made to realize combined apparatuses capable of serving for more than one purpose.

For example, a surgical forceps is known which in the first place seizes and holds parts of the tissue by means of clamping jaws more particularly for ligating parts of blood vessels and which then permits to apply a clamp at each part by means of an integrated fixing device. However, this instrument cannot serve at the same time for cutting of tissue's parts and the attachment of clamps is not in all cases satisfactory or even applicable (U.S. Pat. No. 2,853,074).

A surgical forceps for clamping and subsequently cutting the vessels is known from U.S. Pat. No. 3,175,556. This forceps permits by means of clamping jaws to squeeze side by side two clamps upon the vessels to be cut and closed and then to dissect or sever the vessels between the two clamps by means of an actuated cutting blade. In this case it would be possible to speak of a triple function namely clamping, ligating and separating. The application of the instrument is nevertheless limited to the closing and separating of vessels. Neither the instrument nor the clamp to be fixed are appropriated for clamping tissue's parts, suturing and cutting in a continuous procedure.

A surgical forceps is also known the clamping jaws of which are corrugated so tht thin tissue lying between them is ondulated such that a suturing needle may be introduced through recesses of the clamping jaws and the ondulated tissue in order to suture the clamped section of the tissue (CH-A-166 352). A cutter mobile along the clamping jaws is further provided for cutting the tissue. The instrument comprises only hand actuated grips for actuating the clamping jaws which supposes that the suturing and cutting procedure have to be conducted manually in the region of the clamping jaws.

There is also known an auxiliary apparatus for surgical suturing which comprises a row of needles which serve to draw in many threads at the same time, each one of said threads being drawn in one needle (U.S. Pat. No. 1,577,054).

SUMMARY OF THE INVENTION

The object of the present invention is to realize an instrument which permits through a new, particularly advantageous combination of functions, a working at all times on a longer section in a working cycle without working in the region of the clamping jaws so that the operation is decisively simplified, safe to perform (no secondary hemorrhage) and accelerated.

According to the present invention there is provided a hysterectomium in form of a multi-purpose instrument with clamping jaws and a locking device for stopping the clamping jaw in a clamping position, characterized in that a stitching device is provided at one side of the clamping jaws for stitching clamped parts of tissue and in that at the other side of the clamping jaws there is provided a mobile cutting blade which is movable from an ineffective open position at the side of one clamping jaws to the region of a counter cutting edge at the other clamping jaw for cutting clamped tissue over a section of the length of the clamping jaws at the side of said clamping jaws.

The device is therefore an instrument or hysterectomium with an integrated clamping, separating and suturing device which permits successive procedures of clamping, suturing and separation such as the ones which are necessary e.g. at the time of a surgical removal of the uterus, whereby the tissue between the uterus and the pelvic wall (parametrium) is clamped together and held for clamping safely the blood vessels comprised in it, then the parametrium at the pelvis side is sutured in a place saving manner without hurting the neighbouring ureter and finally the tissue at the side of the forceps at the side of the uterus is separated. During this procedure the particular difficulties connected with operations at the inside of the body are considered (very narrow operating field, lack of freedom of motion and sight, and so on). The instrument (hysterectomium) in accordance with the invention comprises beside clamping jaws for clamping a cutting blade for separating parts of the tissue and a stitching or suturing device for suturing clamped parts of the tissue. By means of this hysterectomium, sections of the tissue may be clamped, sutured and separated section by section so to speak in one working process and without changing the instrument. The mobile cutting blade is preferably arranged at one side and the stitching device at the other side of the clamping jaws. This permits by steady clamping to stitch at one side and to cut at the other side. Many needles, preferably arranged in a row one behind the other, may be provided as well as a hook for successively drawing the thread through the loops of thread formed at each needle so that a section corresponding to the length of the forceps may be clamped, stitched and separated at all times. A further rationalization of the procedure may be achieved by an interchangeable set of needles inserted in one arm of a stitching lever so that when a clamping, stitching and separating procedure is completed, the old set of needles may be replaced by a new one in which a thread is already drawn in, this permitting to immediately continue the procedure.

The invention will be described further by way of an example of an instrument or hysterectomium specially conceived for the above mentioned removal of the uterus and illustrated in the accompanying drawings.

DESCRIPTION OF THE PREFERRED EMBODIMENT

The illustrated hysterectorium comprises a lower clamping jaw 1 and an upper clamping jaw 2 which are attached to levers (branches) 3, respectively 4. These levers are slewably connected together by means of an axle 5 and they comprise ring grips 6, respectively 7 at their extremities. Both arms 3 and 4 are provided with a locking lug 8, respectively 9 having a catch or locking indentation. They serve for automatically locking the forceps in its compressed condition which permits and facilitate the execution of further manipulations by the surgeon. The forceps corresponds so far largely to known forceps.

The axle 5 bears an actuating lever 10 of a cutting blade 11 provided with a finger grip 12 at the side opposite to the one of the cutting blade 11 under which one can grasp for actuating the cutting device. The finger grip 12 grasps under the actuating lever 4 of the upper clamping jaw which therefore forms an abutment for this finger grip and also for the cutting blade actuated by the finger grip.

Figure 1:
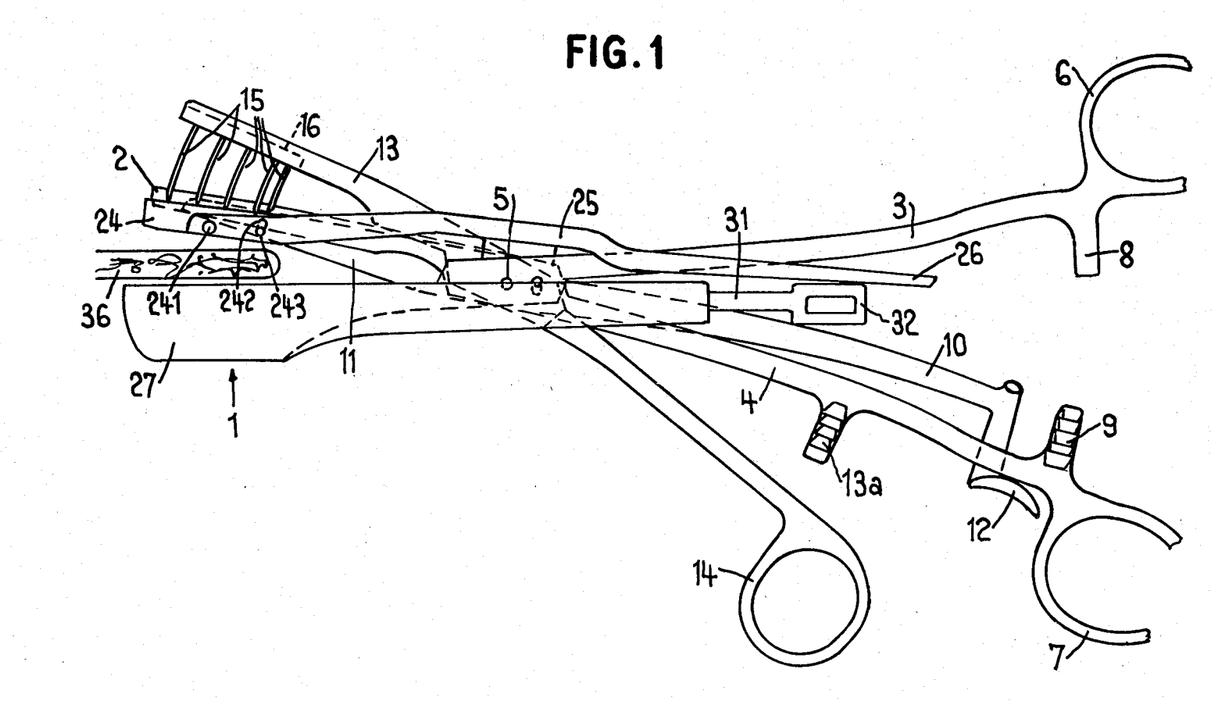
FIG. 1 is a lateral view of the hysterectomium.
Figure 12:
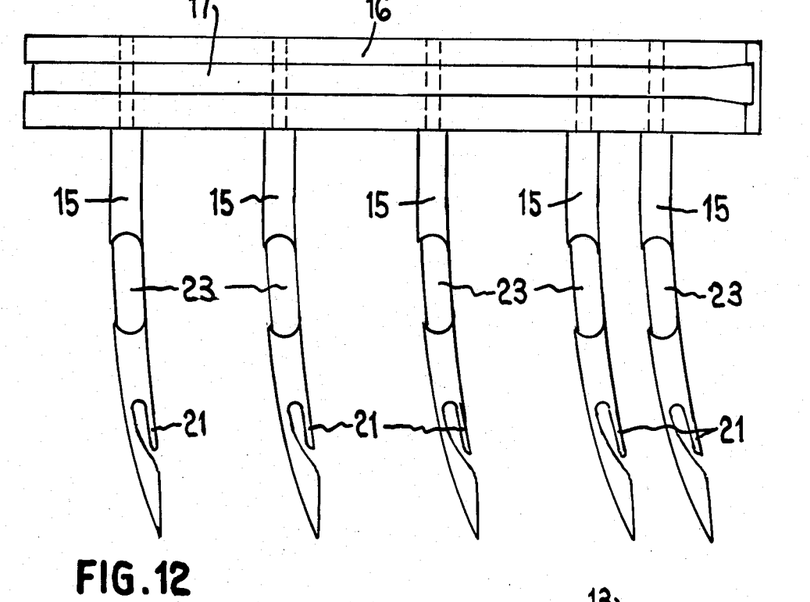
FIGS. 12 and 13 show a lateral and top view of an interchangeable set of needles.

The axle 5 bears also a slewable stitching lever 13 with a ring grip 14. The extremity of the stitching lever 13 opposite to the ring grip 14 bears a set of stitching needles 15 indicated schematically in FIG. 1. The configuration of this set of needles and its mounting in a stitching arm is fully illustrated in FIGS. 12 to 14. The needles 15 are mounted in a flat needle support 16 provided at one side with a groove 17. The groove 17 becomes somewhat larger at the internal extremity of the support 16 in order to facilitate the insertion of the needle support 16. This insertion of the support occurs in a slit 18 at the front end of the stitching lever 13. Two or more pins 19 project laterally in the slit and enter in the groove 17 in order to hold safely the needle support 16 in the slit 18, respectively in the stitching arm 13 and yet the needle support with the needles may be easily extracted toward the front and replaced by another one. The needle support 16 is lightly arcuated in the longitudinal direction so that it fits resiliently against the walls of the groove 17 and it is fastened in the latter. Other fastening means are possible, e.g. by a snap binding.

Figure 2:
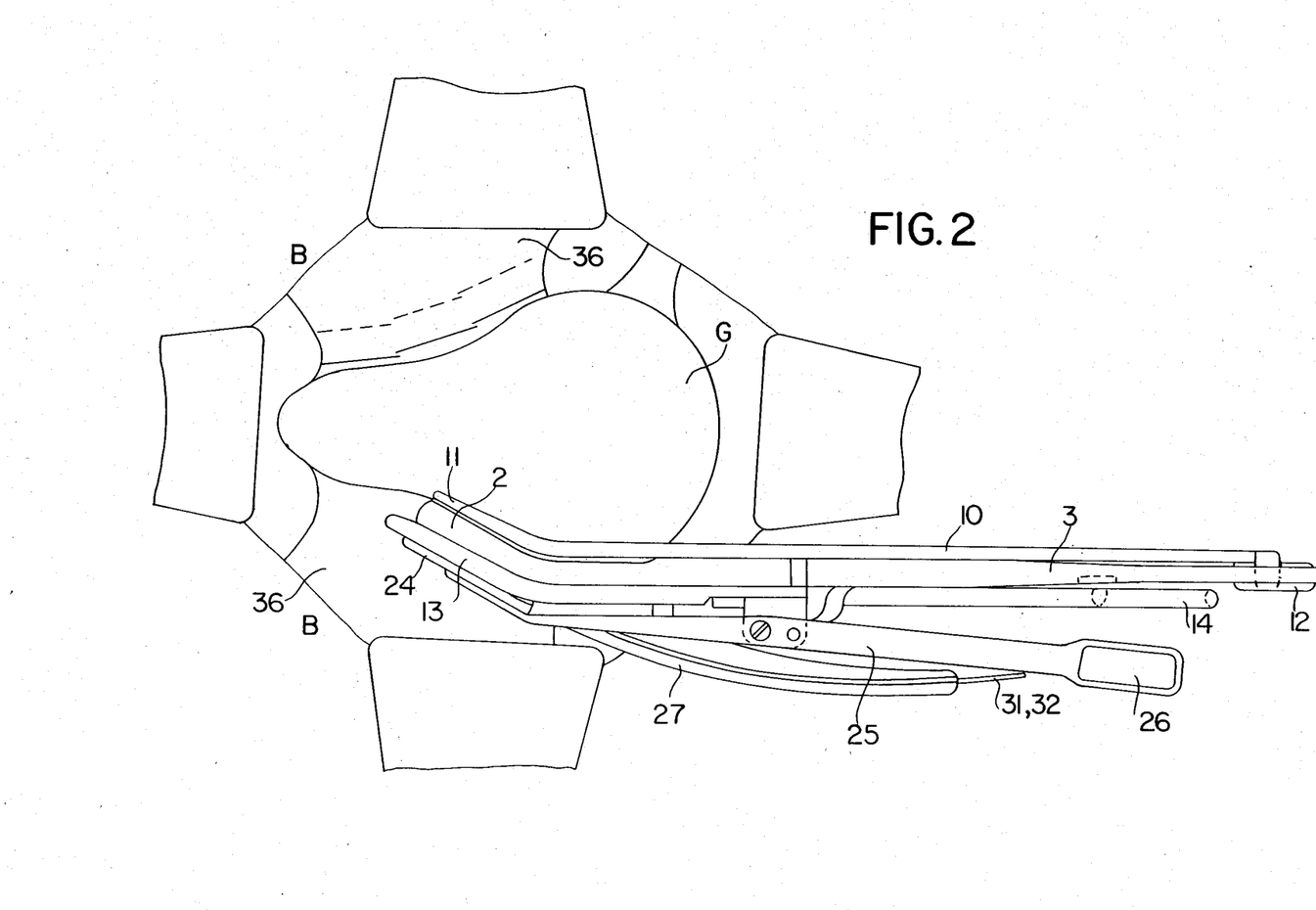
FIG. 2 shows a top view of the instrument with a view of the operation field for a first kind of operation.
Figures 13, 14:
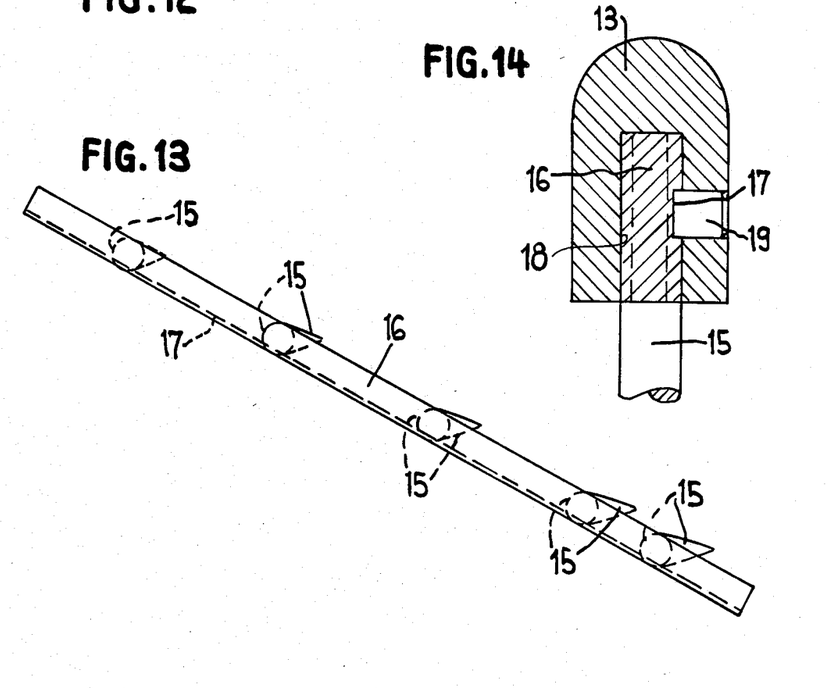
FIG. 14 shows a section through the set of needles and its mounting in a stitching lever.

At least the two internal needles of the set of preferably five needles 15 are arranged closer to each other than the other needles. The reason for this arrangement will be explained later. The needle are arcuated, whereby the center of curvature corresponds each time to the axle 5 and the needles lie in radial planes with respect to the axle 5 as indicated in FIG. 13. Under these circumstances the needles penetrate without relative lateral motion in the parts of the tissue held between the clamping jaws when the stitching lever 13 is swung, and this without causing injuries to the tissue greater than the ones which are absolutely necessary for the suturing procedure. The clamping jaws 1 and 2, the effective part of the cutting blade 11, the end of the stitching lever 13 provided with needles and other parts to be described later are bent by 20° to 30° with respect to the actuating levers which makes the forceps particularly appropriate for its purpose as will be explained later. In other words, the clamping jaws with their actuating levers form an obtuse angle relative to which the cutting blade 11 is at the inside and the stitching device with the needles 15 at the outside (FIG. 2).

Figure 10:
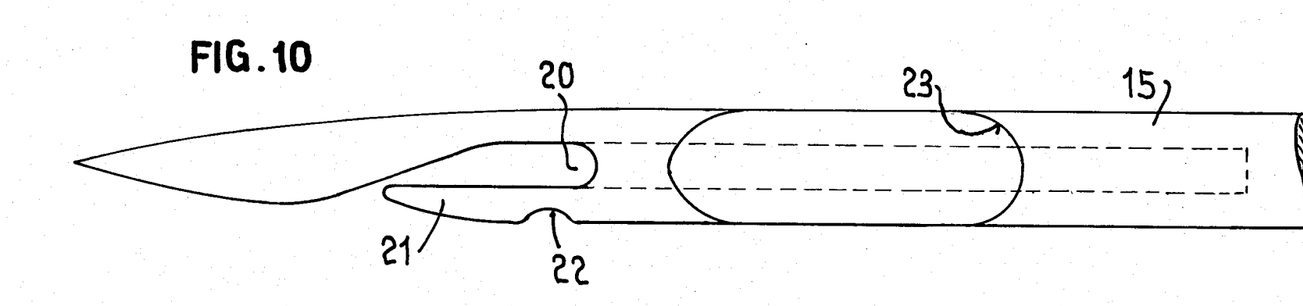
FIGS. 10 and 11 show an enlarged top and lateral view of a needle.
Figure 11:
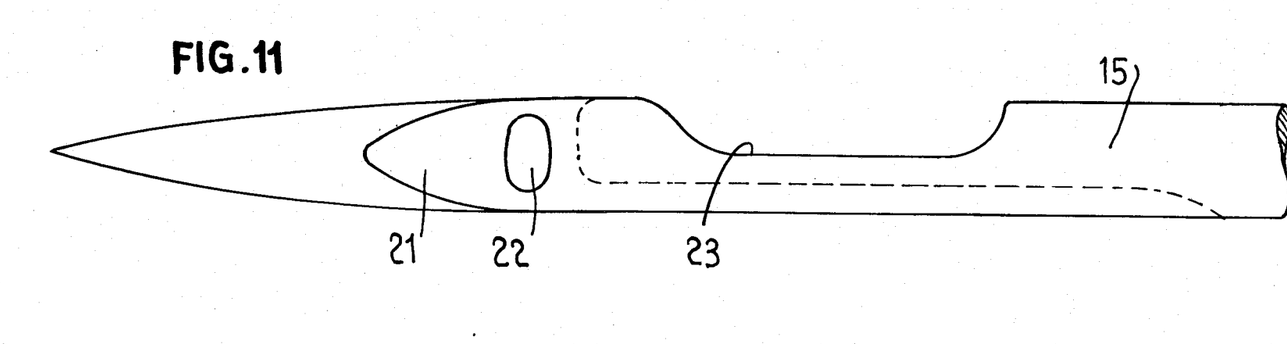

The particular configuration of the needles used in the described embodiment is illustrated in FIGS. 10 and 11. The needles comprise open thread guiding eyes 20 behind their tip having a triangular section. The resiliency of the tongue 21 which narrows the opening of the thread guiding eyes is increased by a place 22 of reduced section. The needle shaft comprises a recess 23 located in a region behind the eye 20, the section at the place of the recess being about half the one of the shaft.

To the set of needles is associated a thread tightener 24 the actuating lever 25 of which is slewable about two axles disposed at right angle to each other so that the thread tightener can execute a swing motion like the one described above for the actuating levers as well as a lateral swing motion for laterally removing the thread tightener outside of the region of the set of needles. The actuation is achieved by the actuating key 26 at the rear end of the lever 25. The thread tigthener 24 is slewably suspended to its actuating lever 25 by means of a pin 241, the swing amplitude being limited by another pin 243 in an elongated hole 242.

Figure 3:
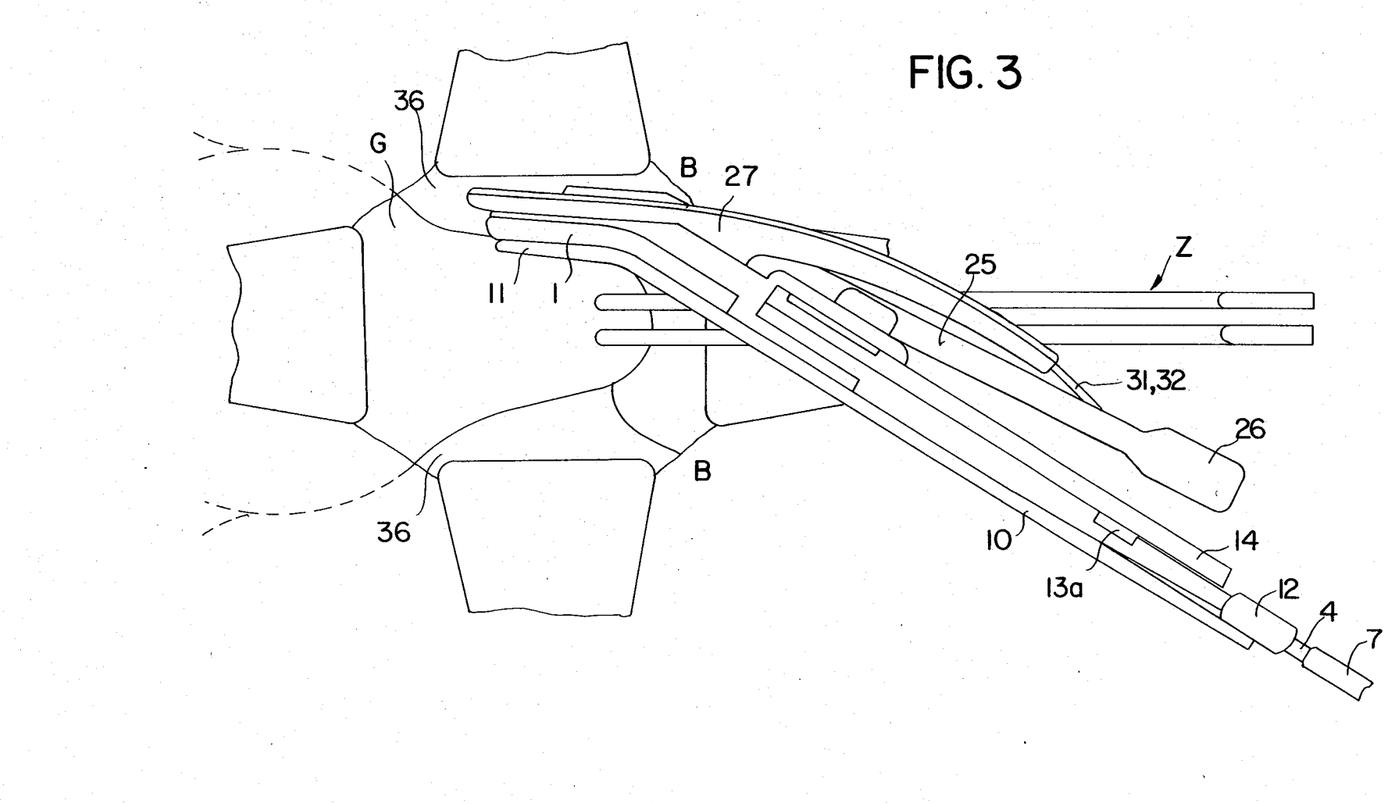
FIG. 3 is a view corresponding to the one of FIG. 2 for a second kind of operation.
Figure 4:
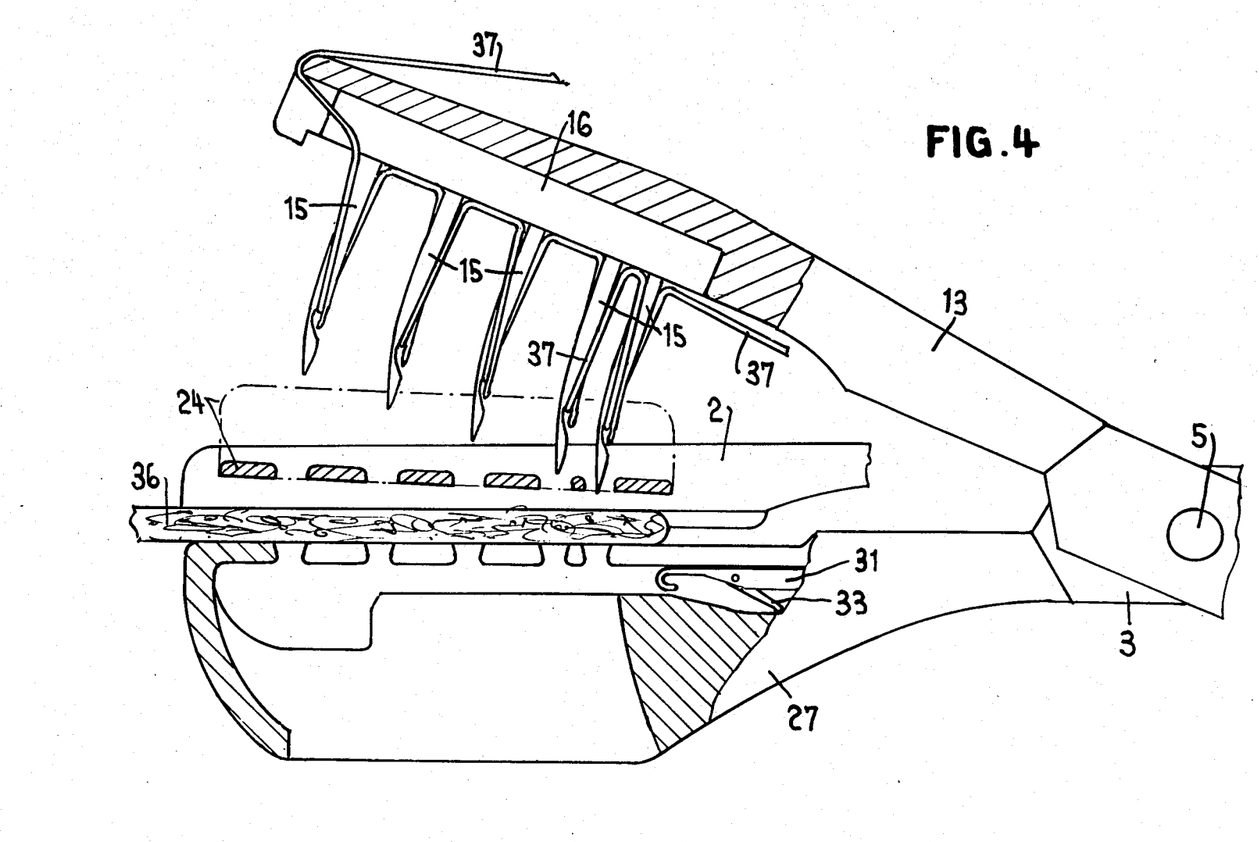
FIGS. 4 to 9 show various steps of the stitching procedure.
Figures 15, 16:
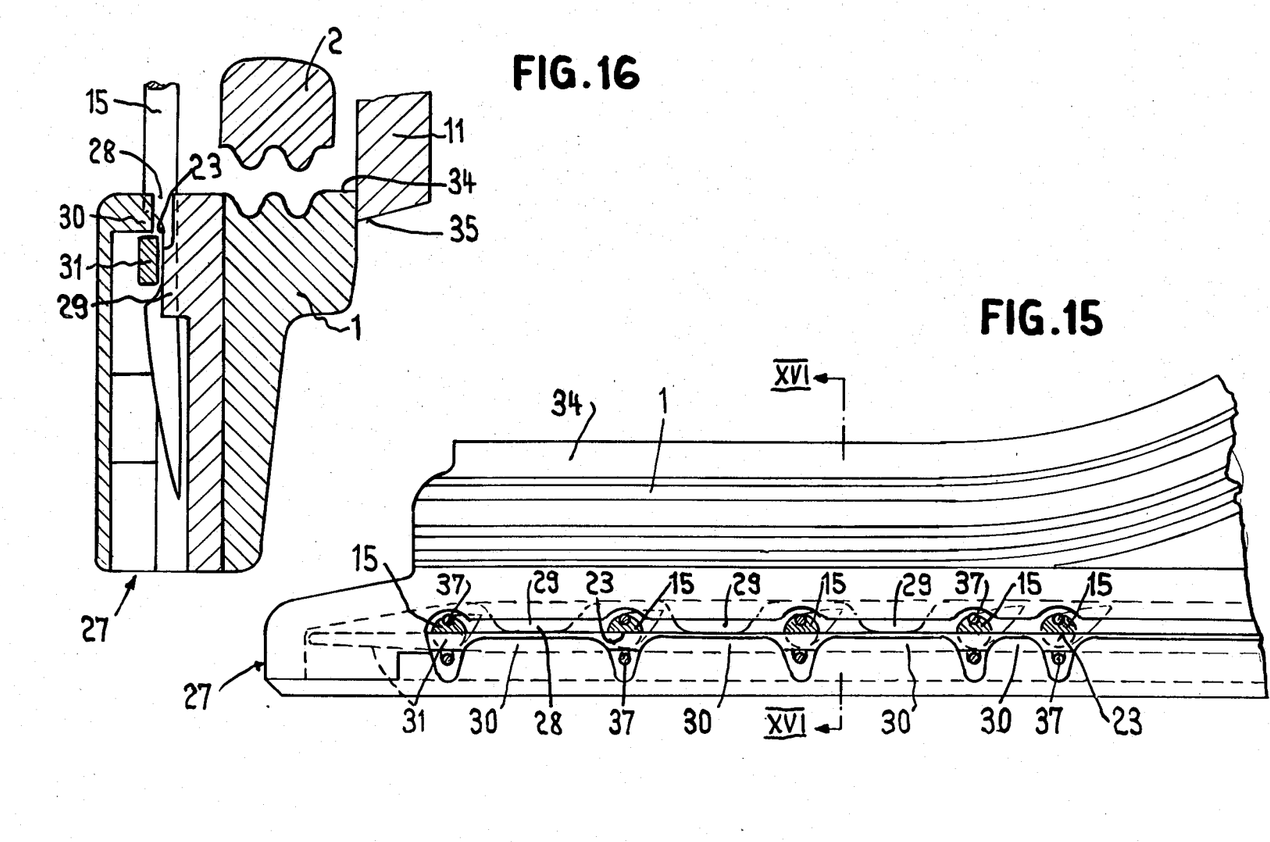
FIG. 15 shows an enlarged top view with the attached part of the stitching device and the section of the needle.
FIG. 16 shows a section along the line XVI—XVI of FIG. 15.

At the side opposite to the one of the cutting blade 11 the lower clamping jaw comprises a case 27 (see FIGS. 15 and 16) in which the needles may penetrate at the time of piercing through the tissue as indicated in FIGS. 15 and 16. The case 27 is in two parts and the edges of the upper walls of these parts have such a configuration that in accordance with FIG. 15 an opening 28 in form of a coherent slit is formed. This opening 28 comprises enlarged places at which the needles 15 penetrate in the case through the opening. Lateral tappets 29 at one of the case parts and overlapping tappets 30 at the other part of the case form a longitudinal guide for a hook 31 which in accordance with FIGS. 1 to 3 projects from the case 27 and comprises an actuating grip 32. The hook 31 is resiliently prestressed so that it lies against the tappet 29, yet it can be displaced into the free space to the left in FIG. 16 under the action of the needles penetrating in the case. A starting position of the hook 31 in accordance with FIG. 4 is determined by a catch not illustrated. As indicated in the FIGS. 4 to 7, the hook comprises a mobile flap 33 which when the hook is inserted in accordance with FIG. 4 is put aside and when the hook is withdrawn in accordance with FIG. 7 the flap is set forwards for closing the eye of the hook. As shown in FIG. 16, the hook is located in the region of the recesses 23 of the needles 15 when the needles are fully introduced in the case 27 so that the needles do not impede a longitudinal motion and displacement of the hook 31.

FIGS. 15 and 16 show the special execution of the clamping jaws with undulated clamping surfaces for increasing the hold of the clamped tissue. One side edge 34 of the lower clamping jaw is grinded to form a cutting edge which cooperates with the cutting edge of the cutting blade 11.

The procedure at the time of an operation, more particularly for the removal of an uterus has been already briefly indicated above. FIGS. 2 and 3 show that the hysterectomium may be used in every case either for an abdominal (laparatomy, FIG. 2) or for a vaginal (FIG. 3) operation. In both cases the parametrium is adjusted by means of blades. For the operation in accordance with FIG. 3, an additional forceps Z is utilized by means of which the uterus G is set in the desired position. At the beginning, the forceps according to the invention is in its open condition according to FIG. 1 which means that the clamping jaws are open and the set of needles 15 with the thread tightener 24 are swung outside of the region of the clamping jaws and the hook is in its starting position (FIG. 4). Then, the tissue (parametrium) between the uterus G and the pelvic wall B which is designated by 36 in the Figures can be seized and clamped by pressing together the clamping jaws 1 and 2 by means of the ring grips 6 and 7 such that the blood vessels comprised in the tissue are safely clamped, after having introduced the open forceps fron one side. The undulated profile of the clamping faces of the clamping jaws as illustrated in FIG. 16 improves the hold of the tissue between the clamping jaws. The latter are held in the pressed together position by the catch of the locking indentations of the lugs 8 and 9 without any other manipulation from the surgeon. The tissue may then be sutured at the side of the clamping jaws at the side of the pelvic wall by actuating the stitching device without producing any gathers or irritation of the uterus.

The suturing procedure is explained by reference to the FIGS. 4 to 9. FIG. 4 shows the starting position. A thread 37 is threaded in the set of needles located in the stitching lever 13, this thread being inserted through every needle eye and adequately attached to the support 16 of the set of needles. The free ends of the thread are long enough for permitting knotting of the thread after the stitching procedure is completed. The front part of the needles has a triangular section for limiting to a minimum the perforations of the tissue produced during the stitching procedure. The set of needles is then swung through the thread tightener 24 and the tissue 36 into the case 27 by actuating the stitching lever 13 by means of the ring grip 14. At this time the hook is still located in the starting position illustrated in FIG. 4 and it does not impede the introduction of the nedles in the case 27. The stitching lever 13 and the set of needles remain then automatically in this position because the stitching lever 13 is locked by a locking indentation 13a of the lever 4 of the upper clamping jaw.

Figure 5:
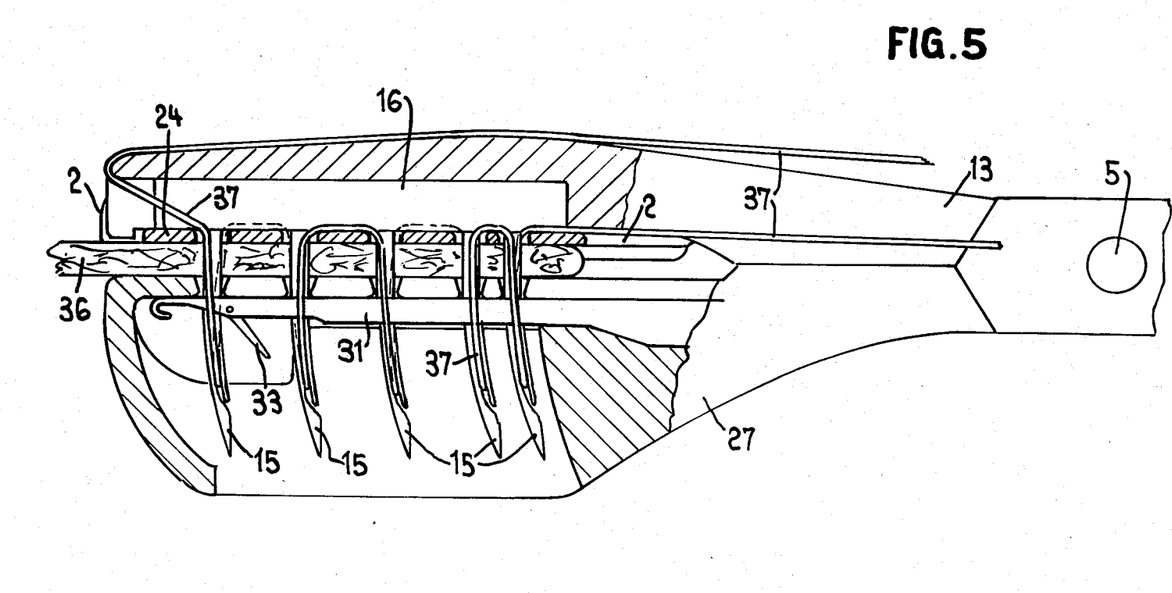
Figure 6:
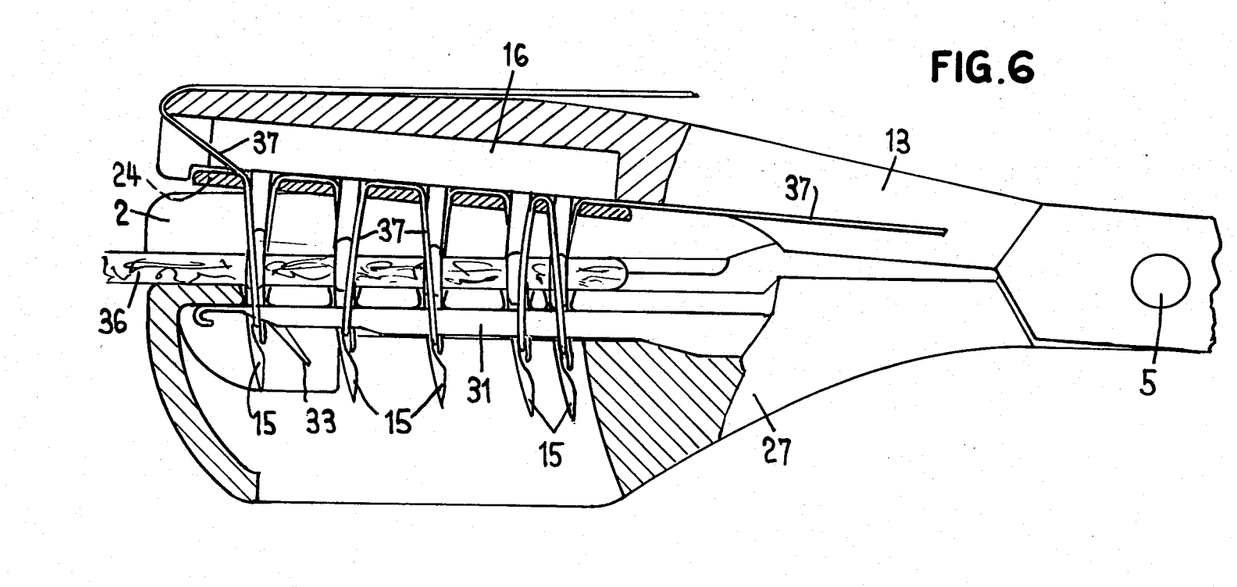
Figure 7:
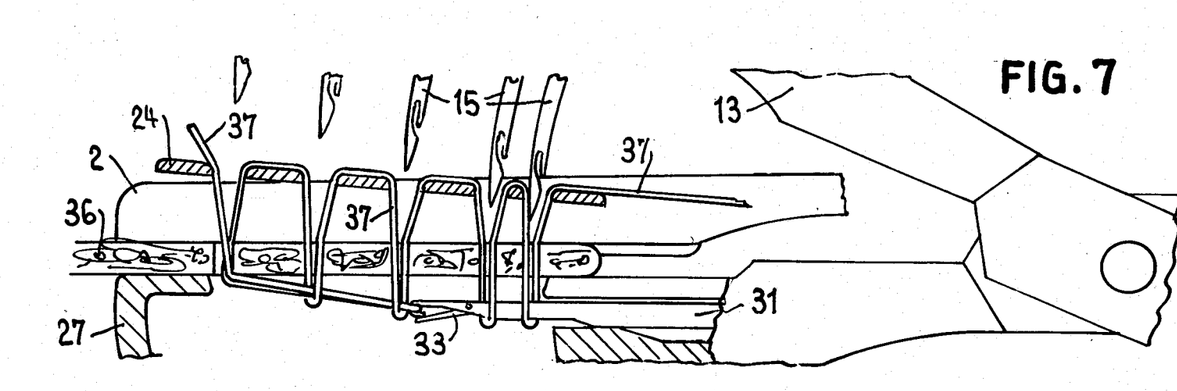
Figure 8:
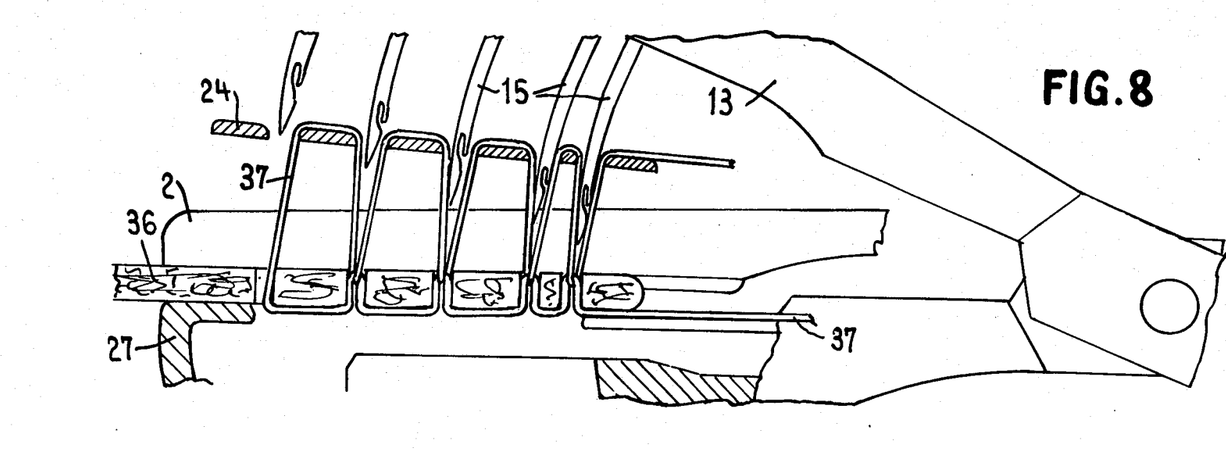
Figure 9:
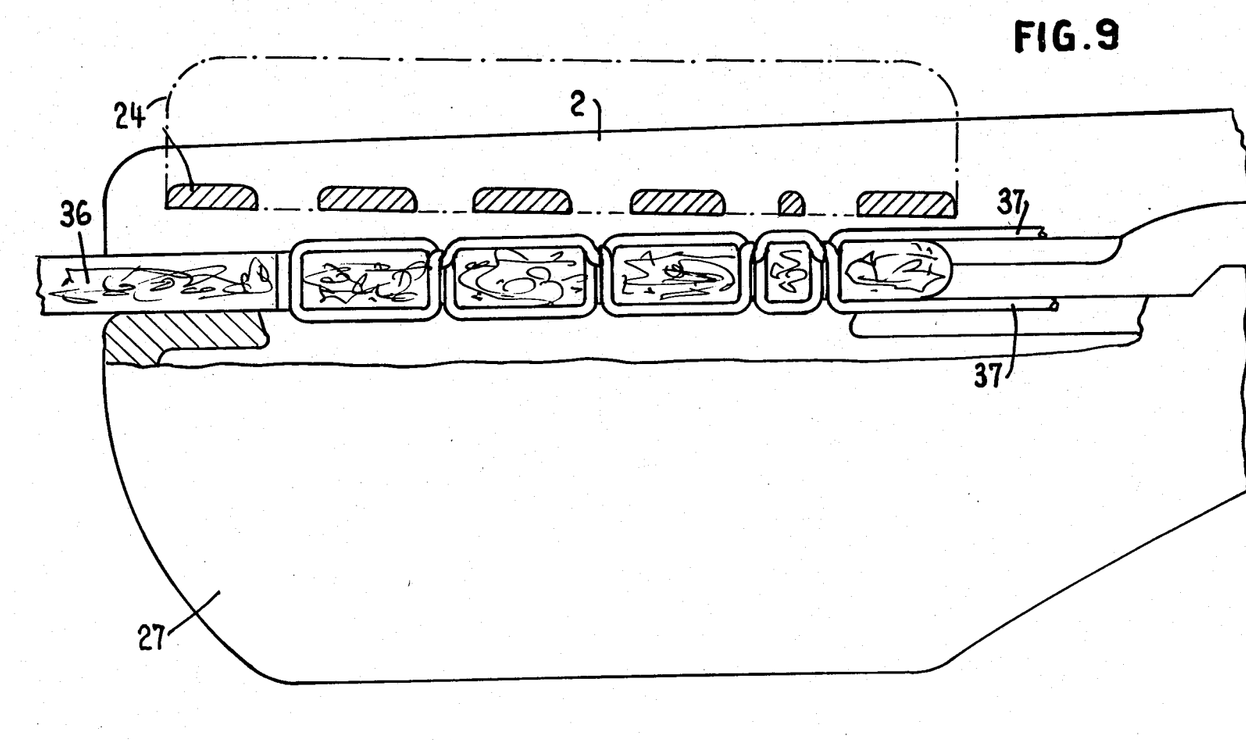

FIG. 5 shows the next step of the stitching procedure. The needles are fully swung in the case 27 and the stitching lever 13, respectively the support of the set of needles inserted in this lever presses the thread tightener 24 regularly on the tissue 36 because of its slewability. At this stage, the hook 31 may be advanced immediately alongside of the needles in the front position illustrated in FIG. 5 by means of its grip 32. The ends of the thread 37 are laid toward the rear. Then the set of needles and the thread tightener 24 are somewhat lifted in the position illustrated in FIG. 6, whereby the needles are partially withdrawn from tissue 36 and the thread loops are laid about the resilient hook which has moved aside, these loops fitting closely to the lower side of the hook. The hook is then withdrawn as indicated in FIG. 7, whereby the foremost thread loop is seized by the hook. At the latest when the flap 33 runs against the thread loop of the second needle, this flap is laid toward the front and it forms together with the hook a closed eye in which the foremost thread loop is held but which does not contain the other thread loops. The foremost thread loop, respectively the thread end which is taken along by the withdrawal of the hook is thus drawn through the remaining thread loops as indicated in FIG. 7, whereby during this procedure the set of needles is preferably placed in its ineffective position. In this manner, the liberated hook 31 comes back resiliently in its starting position at the tappet 29 (FIG. 16). It is finally fully pulled out rearwards. Then, the thread tightener 24 is lifted according to FIG. 8 and it pulls in the thread lying under the tissue so far in the tissue that the entwinements between the upper and the lower part of the thread come to lie at the upper side of the clamped tissue 36. The slewability of the thread tightener ensures a regular stretching of every loops. Then, the upper thread end is tightened so far that the thread tightener comes to lie upon the tissue. Then, the thread tightener is swung to the side about its second axle and the remaining short free lying upper thread loops can be tightened without entanglement by pulling on the thread end which leads to the situation according to FIG. 9. The perforations in the tissue are closed by the thread knots. The two thread ends are then knotted together so that a certain section of the separated parametrium at the pelvic wall side is firmly sutured. The parametrium is then separated at the side of the uterus by actuating the cutting blade 11. The clamping jaws are opened by spreading to the side the arms 3 and 4 and therewith disengaging the locking indentation at the lugs 8 and 9 so that the forceps is ready for a further suturing and separating procedure at a nearest section. The old set of needles is pulled out toward the front and a new one comprising a set of needles provided with the thread is inserted. The hook is placed again in the starting position (FIG. 4). The instrument is therewith ready for clamping, suturing and separating of the next section. These procedures are repeated until the whole parametrium is separated and sutured. As indicated in the upper part of FIG. 2, the sections of suturing and of separation may be slightly shifted and they may also overlap. As indicated in FIG. 7, the foremost thread loop, respectively the thread end connected with it is pulled through under the cover of the case 27 by the hook. The above described through opening 28 yet permits to pass the thread freely upwards which means that no difficulties arise with respect to the guiding of the thread. The reason for which the two rearmost needles are disposed at a closer distance to each other than the other needles is that the closer stitches at the rear end of the suturing section at which the thread ends are knotted must render more difficult a free loosening of the suture. As the case may arise it would also be possible to avoid the knotting of the thread ends, especially when more than two needles at a closer distance are provided.

The invention is not limited to the illustrated embodiment. For other kinds of operations, particulars of the instrument can be executed differently. More particularly, the set of needles may comprise more or less needles and it can be longer or shorter, whereby the length is obviously limited by the forces to be applied. The needles may comprise resilient closing flaps for the eyes instead of a narrowed entrance opening in the eye 20. The active parts of the forceps may be quite straight or bent in another direction with respect to the actuating levers.

The above described embodiment represents an optimal solution in the sense that the clamping, suturing and separating devices are integrated which permits a particularly simple and safe working due to the fact that the suture and the cut are precisely positioned and dimensioned with respect to the clamped parts of the tissue. Yet, a simplified instrument without stitching device is also very advantageous because it permits simplifying considerably the clamping and cutting procedure. On the other side, the cutting device could also be omitted which would lead to an instrument capable of holding the tissue and of suturing it rationally on the clamped length. Finally, only the stitching elements could be present.

We claim:

1. Hysterectomium in form of a multi-purpose instrument with clamping jaws and a locking device for stopping the clamping jaws in a clamping position, characterized in that a stitching device is provided at one side of the clamping jaws for stitching clamped parts of tissue over a section of the length of the clamping jaws and in that at the other side of the clamping jaws a mobile cutting blade is provided which is movable from an ineffective open position at a side of one clamping jaw to a region of a counter cutting edge at the other clamping jaw for cutting tissue over a section of the length of the clamping jaws at the said other side of the clamping jaws.

2. Hysterectomium according to claim 1, wherein in the ineffective position of the cutting blade, a cutting edge of said cutting blade is protected by lying close at one side of one clamping jaw.

3. Hysterectomium according to claim 1, whereby the clamping jaws with slewable actuating arms connected to them enclose an obtuse angle, characterized in that the cutting blade is arranged at the inside and the stitching device at the outside relative to said angle.

4. Hysterectomium according to claim 1, wherein the stitching device comprises a plurality of needles and a hook for the entwinement of a suturing thread.

5. Hysterectomium according to claim 4, wherein the stitching device further comprises a mobile thread tightener actuable in the stitching direction of the needles and in a direction perpendicular thereof.

6. Hysterectomium according to claim 5, wherein the thread tightener comprises an actuating lever slewably connected to said hysterectomium whereby a regular stretching of the thread is obtained.

7. Hysterectomium according to claim 5, wherein an interchangeable set of needles is inserted in one arm of a stitching lever.

8. Hysterectomium according to claim 7, wherein the set of needles is held in a needle support, said needle support being held with a resilient initial tension in the stitching lever.

9. Hysterectomium according to claim 7, wherein the needles lie in radial planes of the swivelling axle of the stitching lever, said needles having a curvature the center of which coincides with the swivelling axle.

10. Hysterectomium according to claim 4, wherein at one side of one of the clamping jaws there is provided a case in which the needles can enter through an openworked cover and in which the hook is slidingly guided.

11. Hysterectomium according to claim 10, wherein the hook fits closely and resiliently against the side of the needles and wherein the hook may move away from said needles in a direction perpendicular thereto.

12. Hysterectomium according to claim 10, wherein the cover comprises an opening with enlargements at for passage the needles.

13. Hysterectomium according to claim 4, wherein each of the needles comprise an open eye with a narrowed opening.

* * * * *